(12) United States Patent
Duran Lopez et al.

(10) Patent No.: US 8,288,394 B2
(45) Date of Patent: Oct. 16, 2012

(54) 1-(1H-1,2,4-TRIAZOL-1-YL)BUTAN-2-OL DERIVATIVE FOR PHARMACEUTICAL USE, AND THE USE OF A 1-(1H-1,2,4-TRIAZOL-1-YL)BUTAN-2-OL DERIVATIVE WITH SUBSTANTIALLY UNDEFINED CRYSTAL SHAPE FOR PREPARING SAID 1-(1H-1,2,4-TRIAZOL-1-YL)BUTAN-2-OL DERIVATIVE

(75) Inventors: Ernesto Duran Lopez, Castellbisbal (ES); Juan Contreras Lascorz, Celrá (ES)

(73) Assignee: Medichem, S.A. (ES)

( * ) Notice: Subject to any disclaimer, the term of this patent is extended or adjusted under 35 U.S.C. 154(b) by 80 days.

(21) Appl. No.: 12/842,540

(22) Filed: Jul. 23, 2010

(65) Prior Publication Data

US 2011/0159096 A1 Jun. 30, 2011

Related U.S. Application Data

(60) Provisional application No. 61/290,929, filed on Dec. 30, 2009.

(51) Int. Cl.
*A01N 43/54* (2006.01)
*C07D 239/42* (2006.01)
*C07D 401/04* (2006.01)

(52) U.S. Cl. ........................ 514/256; 544/333
(58) Field of Classification Search .................. 514/256; 544/333
See application file for complete search history.

(56) References Cited

U.S. PATENT DOCUMENTS

| | | | |
|---|---|---|---|
| 6,558,435 | B2 | 5/2003 | Am Ende et al. |
| 6,586,594 | B1 | 7/2003 | Butters et al. |
| 2004/0098839 | A1 | 5/2004 | Brenek et al. |
| 2005/0112204 | A1 * | 5/2005 | Humphrey et al. ............ 424/486 |
| 2008/0194820 | A1 * | 8/2008 | Sundaram et al. ............ 544/333 |

FOREIGN PATENT DOCUMENTS

| | | |
|---|---|---|
| EP | 0 440 372 B1 | 6/1993 |
| EP | 1 157 726 A1 | 11/2001 |
| WO | WO 2006-065726 A2 | 6/2006 |
| WO | WO 2007-132354 A2 | 11/2007 |
| WO | WO 2007132354 A2 * | 11/2007 |
| WO | WO 2008-075205 A2 | 6/2008 |

OTHER PUBLICATIONS

IP.com Electronic Publication, IPCOM000125373D (May 31, 2005).*
L.J. Taylor et al., 8 Organic Process Research and Development, 674-679 (2004).*
Liversidge et al., 125 International Journal of Pharmaceutics, 91-97 (1995).*
D. G. Shlieout et al., 3 AAPS PharmSciTech, 4 (2002).*
S.J. Roffey et al., "The Disposition of Voriconazole in Mouse, Rat, Rabbit, Guinea Pig, Dog, and Human," *Drug Metab Dispos.* 2003, vol. 31, pp. 731-741.
N. Rasenack et al., "Micron-Size Drug Particles: Common and Noval Micronization Techniques," *Pharm Dev. Technol.*, vol. 9, 2004, pp. 1-13.
Jun-Ici Jinno et al., "Effect of particle size reduction on dissolution and oral absorption of a poorly water-soluble drug, cilostazol, in beagle dogs," *J. Control. Release*, 2006, 111, pp. 56-64.
L.J. Taylor et al., Predictive Milling of Pharmaceutical Materials Using Nanoindentation of Single Crystals, *Organic Process Research & Dev.*, vol. 8, No. 4, 2004, pp. 674-679.
IP.com Journal, 2005, 5, 38 (No. IPCOM000125373D).
F.M. Barreiros et al., "Calculating Shape Factors from Particle Sizing Data," *Part. Part. Syst. Charact.*, 1996, vol. 13, pp. 368-373.
Encapsulated and powdered foods, CRC Press 2005 (p. 49).
F.M. Richards, et al., Determination of the density of solids, *International Tables for Crystallography*, Springer, 2006 (p. ?).
K. Ravikumar et al., "Vorizonazole, an antifungal drug," Acta Cryst., 2007, pp. 565-567.
European Pharmacopoeia 6.6, "2.9.36 Powder Flow," Jan. 2010, pp. 5107-5109.
Y. Qiu et al., "Developing Solid Oral Dosage Forms," *Pharmaceutical Theory & Practice Academic Press*, 2009, pp. 169-170.
J.C. Ramirez-Dorronsoro et al., "Chargeability Measurements of Selected Pharmaceutical Dry Powders to Assess their Electrostatic Charge Control Capabilities," *AAPS PharmSciTech*, vol. 7, 2006, Article 103, pp. E1-E8.
S.L. Soo, *Instrumental for fluid-particle flow*, Noyes Publications 1999, p. 64.
S. Brunauer et al., "Adsorption of Gases in Multimolecular Layers," *J. Am. Chem. Soc.*, 1938, 60, pp. 309-319.
D.L. Black et al., Laser-Based Techniques for Particle-Size Measurement: A Review of Sizing Methods and Their Industrial Applications, *Progress in Energy and Combustion Science*, vol. 22, No. 3, Jan. 1, 1996, pp. 267-306, XP004068954.

* cited by examiner

*Primary Examiner* — James O Wilson
*Assistant Examiner* — Alexander R Pagano
(74) *Attorney, Agent, or Firm* — Leydig, Voit & Mayer, Ltd.

(57) ABSTRACT

The present invention relates to voriconazole, processes of preparing voriconazole, and pharmaceutical compositions and therapeutic uses thereof. In particular, the present invention also relates to voriconazole prepared from voriconazole having a substantially undefined shape and/or crystal habit. The invention further relates to voriconazole having a modified sphericity factor and/or specific surface area and/or Sauter diameter compared to voriconazole known from the prior art.

40 Claims, 6 Drawing Sheets

1-(1H-1,2,4-TRIAZOL-1-YL)BUTAN-2-OL DERIVATIVE FOR PHARMACEUTICAL USE, AND THE USE OF A 1-(1H-1,2,4-TRIAZOL-1-YL)BUTAN-2-OL DERIVATIVE WITH SUBSTANTIALLY UNDEFINED CRYSTAL SHAPE FOR PREPARING SAID 1-(1H-1,2,4-TRIAZOL-1-YL)BUTAN-2-OL DERIVATIVE

CROSS-REFERENCE TO RELATED APPLICATIONS

This patent application claims the benefit of U.S. Provisional Patent Application No. 61/290,929, filed Dec. 30, 2009, which is incorporated by reference.

BACKGROUND OF THE INVENTION

The present invention is concerned with voriconazole, processes of preparing voriconazole, and pharmaceutical compositions and therapeutic uses thereof. In particular, the present invention is concerned with a voriconazole product prepared from voriconazole with substantially undefined crystal shape and/or crystal habit and as such the provision of voriconazole according to the present invention with modified specific surface area and/or Sauter diameter and/or as appropriate sphericity factor compared to voriconazole known from the prior art.

Voriconazole is an active pharmaceutical substance with an empirical formula of $C_{16}H_{14}F_3N_5O$ and a molecular weight of 349.31. Voriconazole is the international commonly accepted non-proprietary name for (2R,3S)-2-(2,4-difluorophenyl)-3-(5-fluoropyrimidin-4-yl)-1-(1H-1,2,4-triazol-1-yl)butan-2-ol, which is represented by Formula (I):

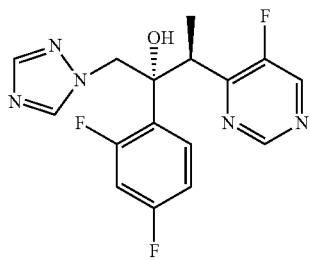

(I)

Voriconazole is a commercially marketed pharmaceutically active substance known to be useful for the treatment of some fungal infections. In the United States, voriconazole is marketed under the trademark VFEND™. The VFEND™ products are available as an I.V. solution, a powder for oral suspension (and hence an oral suspension), and film coated tablets for oral administration.

Voriconazole is disclosed in European Patent EP 0440372B1. Precisely, in Example 7 of EP 0440372B1, the final product voriconazole is obtained as a crystalline solid, showing a melting point of 127° C. and a specific optical rotation of −62° (c=1 mg/mL).

A problem associated with the use of voriconazole is that voriconazole is practically insoluble in water. Specifically, in *Drug Metab. Dispos.* 2003, 31, 731, an aqueous solubility of 0.7 mg/mL is reported for voriconazole, which corresponds to a very slightly soluble drug based on the US Pharmacopeia.

The drug absorption rate of poorly water-soluble drugs (i.e., drugs with solubility below 1 mg/mL) can be particularly affected by the particle size because, for these drugs, the bioavailability is dissolution rate-controlled in most cases (*Pharm. Dev. Technol.* 2004, 9, 1-13). On this basis, mechanical milling is a common technique to enhance dissolution of poorly water-soluble drugs (*J. Control. Release,* 2006, 111, 56). However, in *Org. Process Res. Dev.* 2004, 8, 674, it is mentioned that voriconazole is very plastic and difficult to mill and that no size reduction below 250 μm is generally not achieved using standard milling conditions.

There are a number of references in the literature describing processes to obtain voriconazole with small particle size distribution.

U.S. Pat. No. 6,558,435 B2 describes a method of preparing and crystallizing pharmaceutical products, e.g., ziprasidone and voriconazole, by using fluid jet streams and which directly produces high surface area product crystals. Precisely, Example 4 of U.S. Pat. No. 6,558,435B2 describes a process of preparing and crystallizing voriconazole with controlled particle size by a technique consisting of mixing a solution of voriconazole (1R)-(−)-10-camphorsulfonate in a mixture 50:50 volume ratio of ethanol/water with another solution of a base (i.e., aqueous solution of sodium acetate) in such a way that both solutions are conducted separately through individual jets and contacted as jet streams in a vessel. It is described that the voriconazole particles provided in Example 4 of U.S. Pat. No. 6,558,435B2 showed, after sieving through a 600 μm screen, a volume mean diameter D[4,3] of 22 μm, a D[v,0.9] of less than 41 μm, and a D[v,0.5] of less than 18 μm, as measured by dry particle sizing analysis (SympaTec). It is also mentioned that the specification of product conventionally obtained by jet milling is 90% less than 130 μm and 50% less than 50 μm.

There are a number of problems associated with understanding what is actually disclosed by U.S. Pat. No. 6,558,435B2, and indeed the disclosure is such that it is not possible to meaningfully evaluate the contribution U.S. Pat. No. 6,558,435B2 makes to the state of the art. Firstly, the above particle size measurement technique of U.S. Pat. No. 6,558,435B2 is a specialized technique and the measurements obtained thereby cannot be compared to the more standard Malvern particle size measuring techniques as hereinafter described in greater detail for the present invention. What this specifically means in the context of the present invention is that the particle size measurements of U.S. Pat. No. 6,558,435B2 cannot in any meaningful way be correlated to the specific particle size measurement provided hereinafter for the present invention. Secondly, the level of disclosure provided by U.S. Pat. No. 6,558,435B2 is non-enabling and cannot be independently repeated so as to render possible any subsequent comparison and evaluation of the disclosure provided thereby. This is because, for example, the equipment disclosed therein (see FIGS. 1 and 2) is not commercially available standard equipment. Also, the technique used therein for measuring the particle size is not sufficiently disclosed. Namely, Example 4 of U.S. Pat. No. 6,558,435B2 only discloses that the particle size analysis was carried out by dry analysis using Sympatec particle size analyzer but does not disclose the specific Sympatec analyzer employed. In this regard, there are a number of Sympatec analyzers available, and the selection of a specific instrumentation will define the technique used for the characterization of the particle size [i.e., Laser Diffraction (LD), Ultrasonic Extinction (USE), Image Analysis (IA) and Photon Cross Correlation Spectroscopy (PCCS)], and each technique will provide different non comparable particle size values. Also, for dry analysis, a specific dry dispersion unit must be selected from the dry dispersion units available from Sympatec. Thirdly, based on the specialized equipment disclosed in U.S. Pat. No. 6,558,435B2 and also the lack of enabling disclosure associated therewith, to the extent that U.S. Pat. No. 6,558,435B2 can be understood it can be seen that the crystallization method as described in U.S. Pat. No. 6,558,435B2 is based on jet streams and requires the use of special equipments and installations. Such equipment and associated installation would make the process of U.S. Pat. No. 6,558,435B2 uneconomical and not suitable for industrial production.

International Patent Application WO 2007/132354 describes a method of obtaining voriconazole with small particle size distribution, with small particle size distribution, in other words characterized by having a particle size distribution wherein about 5-15% of the total volume is made of particles having a diameter of about 6 μm or below, about 45-55% of the total volume is made of particles having a diameter of about 20 μm or below, and about 85-95% of the total volume is made of particles having a diameter of about 40 μm or below, by a crystallization technique consisting of treating voriconazole (1R)-(-)-10-camphorsulfonate in an aqueous solvent with a suitable base at a temperature preferably in the range of room temperature to 55° C., cooling the suspension to a temperature approximately in the range of 20° C. to 25° C., filtering the obtained solid, washing it with water and drying the solid. In particular, Examples 18-23 and 25 of WO 2007/132354 are identified below, together with associated particle size parameters as set out in Table 1.

WO 2007/132354 further describes that the voriconazole can be isolated by treating voriconazole (1R)-(-)-10-camphorsulfonate with a non-chlorinated organic solvent and an aqueous alkaline solution, isolating the organic phase, optionally washing one or more times with water, optionally treating the organic solution with a decolorizing agent, partially distilling the organic solution containing voriconazole, treating the obtained residue with an alcoholic solvent, preferably isopropanol, partially distilling to obtain voriconazole as a residue, and crystallizing the residue from an alcoholic solvent, preferably isopropanol, filtering, and drying. Specifically, Example 24 of WO 2007/132354 describes crystallization from isopropanol, milling, sieving, and blending, thus achieving a particle size distribution again as identified in Table 1. Example 2 of WO 2007/132354 also reports voriconazole after crystallization from isopropanol, but without the particle size reduction techniques disclosed for Example 24, and again particle size parameters for Example 2 are set out in Table 1.

TABLE 1

| Example | Particle Size Distribution (μm) | | | |
| --- | --- | --- | --- | --- |
| | $D_{10}$ | $D_{50}$ | $D_{90}$ | D[4, 3] |
| 2 | 36.9 | 102.4 | 220.0 | a |
| 18 | 4.5 | 16.9 | 37.4 | 18.7 |
| 19 | 5.7 | 208 | 43.4 | 23.3 |
| 20 | 4.2 | 14.9 | 34.1 | 17.5 |
| 21 | 5.3 | 16.7 | 34.1 | 18.3 |
| 22 | 5.2 | 19.1 | 39.1 | 21.0 |
| 23 | 5.2 | 17.9 | 37.5 | 19.8 |
| 24 | 35.9 | 147.6 | 350.0 | a |
| 25 | 5.4 | 17.5 | 37.2 | 19.4 | a Not reported value

It should be noted for WO 2007/132354 that Example 24 is the only specific Example that discloses crystallization from isopropanol followed by particle size reduction, which in general terms are process conditions as employed in the present invention as hereinafter described in greater detail so as to achieve voriconazole with desirable flow characteristics according to the present invention. However, it can be appreciated from Example 24 of WO 2007/132354 and the associated $D_{90}$ as reported in Table 1 above, that particle size as obtained further to Example 24 of WO 2007/132354 does not correspond to particle size as obtained by the present invention substantially as hereinafter described. In this way, it can be further understood that the specific milling conditions employed in WO 2007/132354 do not correspond to the milling, or in more general terms, particle size reduction conditions and/or techniques as employed in accordance with the present invention so as to achieve voriconazole with desirable flow characteristics substantially as hereinafter described in accordance with the teaching of the present invention.

Furthermore, it is also confirmed that the crystallization methods provided in either U.S. Pat. No. 6,558,435B2 or WO 2007/132354 for preparing voriconazole with small particle size distribution do not disclose the specific surface area of the voriconazole obtained after such crystallization processes. In this regard, it is established and well understood in the field of particle size measurement that particle size and/or particle size distribution cannot be directly related to the specific surface area of particles, since any assumption about the particle shape and as such specific surface area fails to account for specific surface texture and/or specific surface contours and/or specific surface defects and/or localized surface properties of the particles, any and all of which can have an influence on specific surface area and associated properties.

The surface properties and in particular specific surface area can be strongly affected, for example, by the high energy input associated with mechanical comminution processes for the reduction of particle size. For example, the high energy input can cause a disruption of the crystal lattice on the particle surface and the creation of crystal defects can result in an increased specific surface area when compared to particles having a similar particle size distribution but obtained by a controlled crystallization process. In this respect, crystallization processes are more likely to provide substantially regular shaped crystals. Still further, the regularity of the shape of the crystal obtained by controlled crystallization will depend on several crystallization factors such as the nature of the solvent and the presence of other co-solvents or anti-solvents, the nature and concentration of chemical impurities, the temperature and the concentration of the saturated solution, the aging time of nucleation crystals under supersaturated conditions, the type of stirring and the reactor geometry and dimensions, the rate of cooling, etc. In view of the above, the specific surface area of the crystals of voriconazole provided in either U.S. Pat. No. 6,558,435B2 or WO 2007/132354 can be neither predicted, nor unequivocally reproduced at least in the case of U.S. Pat. No. 6,558,435B2. Additionally, for WO 2007/132354, as hereinbefore explained, particle sizes obtained thereby can be understood to be different from particle sizes as obtained by the present invention substantially as hereinafter described in greater detail.

It should also be noted that while the crystallization methods provided in WO 2007/132354 for preparing voriconazole with small particle size distribution are suitable and effective for laboratory scale operation, when carried out at pilot plant scales the methods require long cooling times and hence prolonged occupancy times of the reactor. Such conditions for pilot plant operation render the processes disclosed in WO 2007/132354 uneconomical and as such not desirable for scale up.

IP.com Journal, 2005, 5, 38 (No. IPCOM000125373D) tackles the need of having micronized voriconazole for processing to voriconazole-containing pharmaceutical compositions. Specifically, in this reference it is disclosed that voriconazole has the ability to crystallize in three different crystal habits (i.e., plate-like crystal habit, needle-like crystal habit, and crystals with undefined shape), and teaches that the voriconazole in plate-like crystal habit is the crystal habit which is micronized to obtain a powder having desirable particle size, specific surface area, and flow characteristics. Further, in this reference the needle-like crystals are described to be undesirable because, for example, filtration of suspensions of such needle-like crystals is said to be difficult, and that bulk material comprising such needle-like crystals can be subject to blocking or bridging in weighing, handling, and conveying equipment. The crystal habit having crystals of undefined crystal shape is shown in the Examples as being obtained by crystallization from a solvent system selected from the group consisting of isopropanol, methyl ethyl ketone/cyclohexane mixture, ethanol/cyclohexane mixture and dimethyl carbonate/cyclohexane mixture, but there is no disclosure or suggestion of micronization thereof in contrast to the favorable micronization of voriconazole in a plate-like crystal habit as follows.

More specifically, the micronized voriconazole suitable for pharmaceutical use which is described in IP.com Journal, 2005, 5, 38 (No. IPCOM000125373D) is prepared by micronization of the voriconazole in a plate-like crystal habit using an air-jet mill. The micronized voriconazole prepared from plate-like crystals of voriconazole shows a particle size of about 40 µm, preferably about 20 µm, and a specific surface area of about 3 $m^2/g$ to 5 $m^2/g$, preferably about 4 $m^2/g$.

U.S. Pat. No. 6,586,594B1 also discloses a process of preparing substituted triazoles and preparation of voriconazole is specifically described in Preparations 2, 4 and 8. Each of these Preparations describe addition of isopropanol to the combined organic extracts, continued distillation (Preparation 2), cooling, granulation, filtration, washing with further isopropanol and drying to provide solid state voriconazole. U.S. Pat. No. 6,586,594B1 does not provide any further teaching as to particle size modification of the thus obtained voriconazole.

Based on the prior art, there is a need for voriconazole with improved properties for pharmaceutical formulation and such voriconazole is now provided by the present invention substantially as hereinafter described in greater detail.

BRIEF SUMMARY OF THE INVENTION

The invention provides voriconazole having a specific surface area of from about 0.5 $m^2/g$ to about 2 $m^2/g$.

The invention also provides voriconazole having a Sauter diameter of from about 4 µm to about 20 µm.

In an embodiment the invention provides voriconazole having a specific surface area of from about 0.5 $m^2/g$ to about 2 $m^2/g$ and having a Sauter diameter of from about 4 µm to about 20 µm.

The invention also provides a process of preparing voriconazole having a specific surface area of from about 0.5 $m^2/g$ to about 2 $m^2/g$ and having a Sauter diameter of from about 4 µm to about 20 µm said process comprising reducing the particle size of voriconazole with a substantially undefined shape and/or crystal habit.

The invention also provides a pharmaceutical composition comprising voriconazole.

The invention further provides a method of treating a fungal infection.

DETAILED DESCRIPTION OF THE INVENTION

Figure 1:
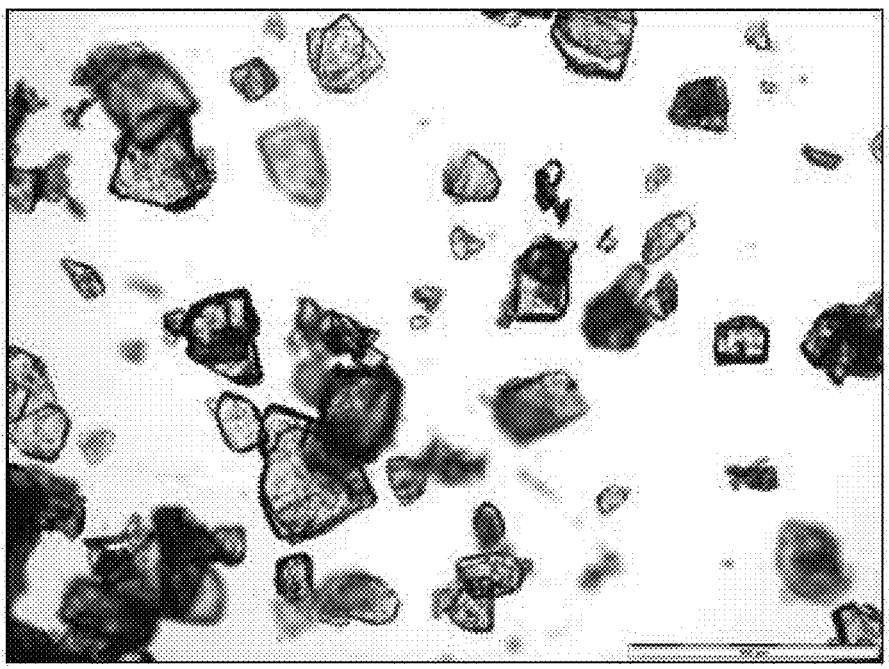
FIG. 1 depicts plate-like voriconazole crystals as obtained in comparative Example 1.
Figure 2:
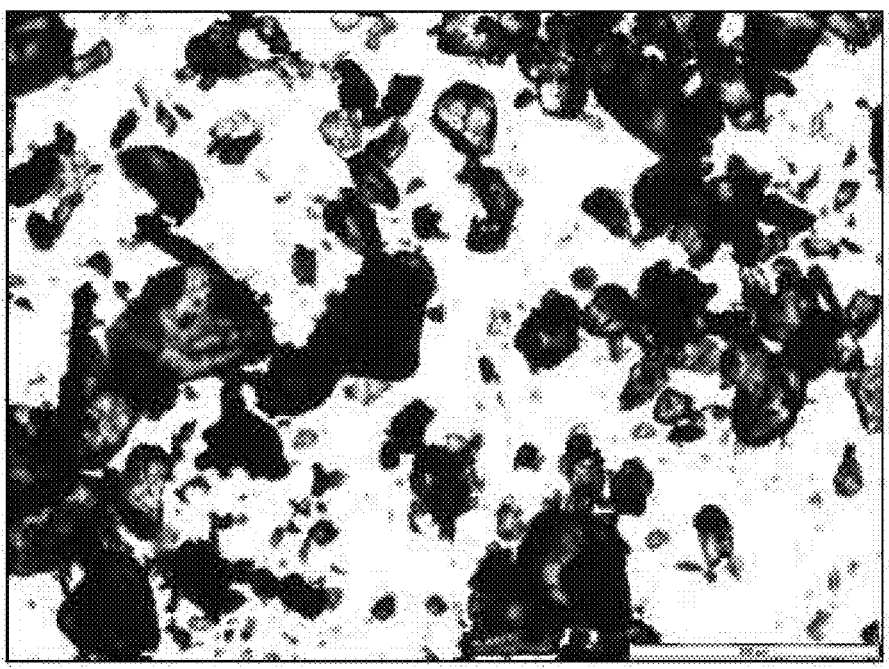
FIG. 2 depicts voriconazole crystals with undefined shape as obtained in Example 1.
Figure 3:
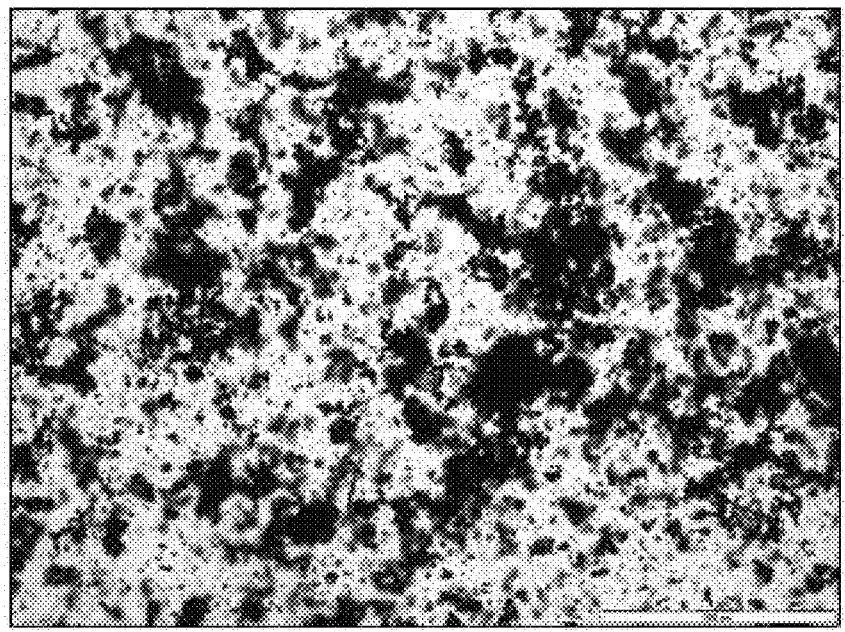
FIG. 3 depicts micronized voriconazole as obtained in Example 2.

There is now provided by the present invention voriconazole with improved properties as compared to the micronized voriconazole described in IPCOM000125373D.

Firstly, the inventors have found that, contrary to what it is described in IPCOM000125373D, the micronized voriconazole obtained from plate-like crystals of voriconazole (as described in IPCOM000125373D) shows undesirable flow characteristics and hence is not desirable for pharmaceutical formulation. In this respect, the inventors have found that the above prior art micronized voriconazole obtained from plate-like crystals has a sphericity ratio of about 0.13. It is recognized that a sphericity factor which is lower than 0.2 indicates low-flowability characteristics and is generally undesirable for pharmaceutical formulation.

Flowability affects the ease with which the material is handled during processing into a pharmaceutical product. When the flowability is poor, problems occur with handling and processing during formulation. It is known that the shape of a particle affects its handling and flow properties. However, quantification of particle shape is extremely difficult for irregular and/or micronized particles. One of the most common ways of expressing the degree of irregularity of the particles is by means of the sphericity factor ($\Psi_W$), which is generally defined as the ratio between the surface area of a sphere having the same volume as the particle and the surface area of the particle:

$$\Psi_W = \frac{d_V^2}{d_S^2}$$

where $d_v$ and $d_s$ are the equivalent volume and surface diameter, respectively (Part. Part. Syst. Charact. 1996, 13, 368-373).

Because sphericity factors are not calculated for each particle but for an assembly of particles, they have to be based on an average size. Thus, the sphericity factor will then be given by the following equation:

$$\Psi_W = \frac{6}{S_W \cdot \rho \cdot D_{MVS}}$$

where $S_W$ is the powder specific surface area, $\rho$ is the particle density and $D_{MVS}$ is the surface area mean diameter, also referred to as the mean volume-surface diameter, the Sauter diameter or D[3,2]. The Sauter diameter is defined as the diameter of a sphere that has the same volume/surface area ratio as the particle of interest. It is important to note that the accuracy of the equation above does not depend on any assumptions, being limited only by experimental conditions.

A sphericity factor of 1.0 describes a perfect sphere with the greatest ease of flow (*Encapsulated and powdered foods*, CRC Press 2005). The more the particles deviate from spheres (i.e., the sphericity factor decreases from 1.0), the stronger the friction and cohesion forces are, which hence results in reduced flowability. In this regard, sphericity factor values below 0.2 are usually found for low-flowability solids in form of platelets or needles. Therefore, a sphericity factor greater than 0.2 generally indicates an acceptable flowing material.

As described in IPCOM000125373D, the micronized voriconazole obtained from a starting material in form of plate-like crystals has a particle size of about 20 μm and a specific surface area ($S_W$) of about 4 m$^2$/g. The inventors have now prepared the micronized voriconazole obtained from plate-like crystals of voriconazole as described in IPCOM000125373D, and have further characterized this prior art voriconazole. Specifically, the prior art micronized voriconazole shows an experimental particle density ($\rho$) of about 1.400 g/cm$^3$, as measured by pycnometry, and a Sauter diameter ($D_{MVS}$) of about 8.3 μm (as described in comparative Example 2 below). The true density of a solid refers to mass of solid material divided by its exact volume without porosity, and can be experimentally measured using a pycnometer, if the crystal structure is not available. However, a more accurate value for the true density can be directly calculated based on the single crystal structure of the compound, as determined by X-ray crystallography (see F. M. Richards, P. F. Lindley, Determination of the density of solids, International Tables for Crystallography, Springer, 2006). Therefore, it is known that the density ($\rho$) of the crystal is a constant value for a specific crystalline form of voriconazole. In this regard, K. Ravikumar et al. in Acta Cryst. (2007), E63, o565-o567, have carried out a single-crystal X-ray study of voriconazole, as obtained from slow evaporation of methanol-water solutions of voriconazole, and report corresponding crystal data. This reported data includes the density of the crystal, which shows a value of 1.442 g/cm$^3$ at 21° C. (294 K). By using this single-crystal data the present inventors have simulated a powder X-ray Diffraction pattern, and have confirmed that the single-crystal data shown in above mentioned Acta Cryst. (2007) corresponds to the same crystalline form of voriconazole as obtained in IPCOM000125373D (referred to herein as voriconazole Form I). In this respect, the inventors also refer to Form I as described in International Patent Application Publication No. WO 2008/075205, and Form B as described in International Patent Application Publication No. WO 2006/065726.

Based on the above, it is understood that the exact crystal density ($\rho$) value of the crystal of voriconazole obtained in IPCOM000125373D is 1.442 g/cm$^3$ at 21° C., as it corresponds to the same crystalline form reported by K. Ravikumar et al. Thus, the micronized voriconazole described in IPCOM000125373D (i.e., obtained from a starting material in form of plate-like crystals) has a sphericity factor of about 0.13 (i.e., below 0.2), as calculated using either the experimental particle density or the more accurate reported crystal density value. Based on the above sphericity value, it can thus be understood that the micronized voriconazole described in IPCOM000125373D (i.e., obtained from a starting material in form of plate-like crystals) shows undesirable flow characteristics and hence is undesirable for use in pharmaceutical formulation.

Additionally, and contrary to what is taught in IPCOM000125373D, the inventors have found that voriconazole with substantially undefined crystal shape and/or crystal habit is a more suitable starting material for preparing micronized voriconazole, since the micronized voriconazole obtained shows improved flowability properties as compared to the micronized voriconazole described in IPCOM000125373D, while essentially maintaining its solubility properties. Thus, the inventors have found that, contrary to the teaching of IPCOM000125373D, voriconazole crystals with substantially undefined crystal shape and/or crystal habit are more preferred than voriconazole crystals in a plate-like habit as a starting material for micronization, since the use of voriconazole crystals with substantially undefined crystal shape and/or crystal habit provides micronized voriconazole with enhanced properties.

As used herein, the wording "substantially undefined crystal shape and/or crystal habit" denotes crystals which are not needle or plate like crystals as described and prepared in IPCOM000125373D. Such "substantially undefined crystal shape and/or crystal habit" can be further understood by reference to its process of preparation and in particular the specific crystallization solvent employed which facilitates the formation of such crystals of "substantially undefined crystal shape and/or crystal habit." Specifically, therefore, voriconazole of "substantially undefined crystal shape and/or crystal habit" as herein described can be further characterized as voriconazole crystallized from a solvent system selected from the group consisting of isopropanol, methyl ethyl ketone/cyclohexane mixture, ethanol/cyclohexane mixture and dimethyl carbonate/cyclohexane mixture, especially isopropanol, and even more suitably as voriconazole crystallized from isopropanol as a crystallization solvent employing a process substantially as described in Example 1 herein or as described in IPCOM000125373D. By exhibiting a "substantially undefined crystal shape and/or crystal habit" it can be further understood that voriconazole employed as a starting material to yield a voriconazole product according to the present invention, can be further characterized as a material comprising a crystal lattice but with an imperfect or undefined outward shape with reference to regular crystal habits already characterized and defined in the art, in particular an imperfect or undefined outward shape with reference to needle or plate like crystals.

Voriconazole with substantially undefined crystal shape and/or crystal habit as referred to above can suitably be employed to prepare voriconazole with improved flowability properties, which can be defined with reference to sphericity factor. According to the present invention, therefore, there is provided voriconazole suitable for pharmaceutical use, characterized by a sphericity factor of at least 0.20, more preferably characterized by a sphericity factor in the range of about 0.20 to 0.70, preferably 0.20 to 0.60, preferably 0.20 to 0.50 and even more preferably characterized by a sphericity factor in the range of about 0.22 to 0.60, or 0.22 to 0.50.

Voriconazole according to the present invention can be still further characterized and distinguished from the prior art by reference to its specific surface area. According to the present invention, therefore, there is still further provided voriconazole suitable for pharmaceutical use, characterized by a specific surface area in the range of from about 0.5 m$^2$/g to about 2 m$^2$/g and more preferably characterized by a specific surface area in the range of from about 0.9 m$^2$/g to about 1.7 m$^2$/g and in some embodiments a specific surface area in the range of from about 0.9 m$^2$/g to about 1.6 m$^2$/g.

In a preferred embodiment, voriconazole according to the present invention is suitable for pharmaceutical use and is characterized by (i) a sphericity factor of at least 0.20 (more preferably a sphericity factor in the range of from about 0.20 to about 0.70 and even more preferably a sphericity factor in the range of from about 0.22 to about 0.60), and (ii) a specific surface area in the range of about 0.5 m$^2$/g to 2 m$^2$/g (more preferably a specific surface area in the range of about 0.9 m$^2$/g to 1.6 m$^2$/g).

Voriconazole according to the present invention can be still further characterized and distinguished from the prior art by reference to its Sauter diameter. According to the present invention, voriconazole suitable for pharmaceutical use is further characterized by a Sauter diameter in the range of from about 4 μm to about 20 μm, and more preferably characterized by a Sauter diameter in the range of from about 12 μm to about 18 μm.

In a further preferred embodiment, there is also provided voriconazole suitable for pharmaceutical use, characterized by (i) a sphericity factor of at least 0.20 (more preferably a sphericity factor in the range of from about 0.20 to about 0.70 and even more preferably a sphericity factor in the range of from about 0.22 to about 0.60), (ii) a specific surface area in the range of from about 0.5 m$^2$/g to about 2 m$^2$/g (more preferably a specific surface area in the range of from about 0.9 m$^2$/g to about 1.7 m$^2$/g), and (iii) a Sauter diameter in the range of from about 4 μm to about 20 μm (more preferably in the range of from about 5 μm to about 18 μm).

In yet a further preferred embodiment, there is also provided voriconazole suitable for pharmaceutical use, characterized by (i) a specific surface area in the range of from about 0.5 m$^2$/g to about 2 m$^2$/g (more preferably a specific surface area in the range of from about 0.9 m$^2$/g to about 1.7 m$^2$/g), and (ii) a Sauter diameter in the range of from about 4 μm to about 20 μm (more preferably in the range of from about 5 μm to about 18 μm).

Suitably voriconazole as provided by the present invention is subjected to mechanical size reduction, and even more preferably can be obtained by micronization, milling or any other method known in the art for mechanically reducing the size of particles (i.e., mechanical comminution), such as cutting, chipping, grinding, crushing, trituration and the like, of voriconazole of substantially undefined crystal shape and/or crystal habit as hereinbefore described. In a preferred embodiment, the present invention provides micronized voriconazole suitable for pharmaceutical use, obtained from voriconazole of substantially undefined crystal shape and/or crystal habit. The term "micronized" as used herein is not intended to limit the scope of the invention to a particular process for the preparation of small particles. The term "micronized" as used herein is thus intended to denote a material formed of small particles, typically voriconazole particles having $D_{90}$ particle size of less than about 250 μm, typically less than about 150 μm and more typically less than about 100 μm. More generally, therefore, and as described above voriconazole small particles according to the present invention can be obtained from any methods known in the art for mechanically reducing the size (i.e., mechanical comminution) of the voriconazole of substantially undefined crystal shape and/or crystal habit as hereinbefore described, which include any one or more of cutting, chipping, grinding, crushing, milling, micronizing, and trituration. Preferably, the voriconazole small particles are obtained from micronization or milling of voriconazole of substantially undefined crystal shape and/or crystal habit as hereinbefore described.

As hereinbefore described, the density (ρ) of a crystal is a constant value for a specific crystalline form of voriconazole. In this regard, voriconazole obtained according to the present invention corresponds to voriconazole Form I, thus showing an X-ray powder diffractogram substantially identical to the X-ray diffractogram described in IPCOM000125373D and hence substantially identical to the simulated X-ray powder diffractogram calculated from the crystal data reported by K. Ravikumar et al. in Acta Cryst. (2007), E63, o565-o567. Thus, the voriconazole according to the present invention can suitably be further characterized by a crystal density value of 1.442 g/cm$^3$ at 21° C., a reported value which is constant for all samples of voriconazole Form I. This reported crystal density substantially as hereinbefore described is based on the crystal structure of voriconazole Form I and as such is understood to be an exact further characterizing value for the voriconazole obtained according to the present invention, which typically corresponds to crystalline Form I. It is also understood that the density of a solid can be experimentally measured using a pycnometer, if the crystal structure is not available. Substantially as hereinbefore described however, the true and accurate density refers to mass of solid material divided by its exact volume without porosity, and it can be directly calculated based on the crystal structure of the compound, as determined by X-ray crystallography (see F. M. Richards, P. F. Lindley, Determination of the density of solids, International Tables for Crystallography, Springer, 2006). Therefore, it is known that the density (ρ) of the crystal is a constant value for a specific crystalline form of voriconazole.

Voriconazole according to the present invention can suitably be further characterized by an experimental particle density in the range of from about 1.300 g/cm$^3$ to about 1.450 g/cm$^3$, more typically a measured experimental particle density in the range of from about 1.320 g/cm$^3$ to about 1.400 g/cm$^3$ and even more typically a measured experimental particle density of about 1.36 g/cm$^3$, which values are measured by pycnometry. As is recognized in the art, values for such measured experimental particle density are likely to have some variation from the above discussed exact characterizing value for density based on crystal structure.

The present invention still further provides a process of preparing voriconazole substantially as described herein comprising: (a) providing voriconazole with a substantially undefined crystal shape and/or crystal habit substantially as hereinbefore described; and (b) reducing the particle size of voriconazole of step (a) (i.e., mechanical comminution) so as to at least modify the sphericity factor and/or specific surface area, and optionally where appropriate also the Sauter diameter and/or $D_{90}$ thereof, thereby providing voriconazole substantially as described herein.

In particular the present invention still further provides a process of preparing voriconazole substantially as hereinbefore described and there is thus provided a process comprising: (a) recrystallizing voriconazole from a solvent system selected from the group consisting of isopropanol, methyl ethyl ketone/cyclohexane mixture, ethanol/cyclohexane mixture and dimethyl carbonate/cyclohexane mixture, especially isopropanol; (b) subjecting the voriconazole of step (a) to mechanical particle size reduction (i.e., mechanical comminution) so as to at least modify the sphericity factor and/or specific surface area, and optionally where appropriate also the Sauter diameter and/or $D_{90}$ thereof, thereby providing voriconazole substantially as hereinbefore described.

Typically, mechanical particle size reduction/comminution as referred to in step (b) comprises cutting, chipping, grinding, crushing, milling, micronizing, or triturating the voriconazole of step (a), preferably comprises milling or micronizing, and typically by carrying out milling comprises air-jet-milling or pin-milling.

Further, the applicants have found that, contrary to the teachings of Org. Process Res. Dev. 2004, 8, 674, in which it is mentioned that voriconazole is very plastic and difficult to mill and as such size reduction below 250 µm is generally not achieved using standard milling conditions, the voriconazole with undefined crystal shape and/or crystal habit substantially as hereinbefore described can be suitably milled using standard milling conditions (i.e., pin-milling at 7,000 rpm) as compared with the micronizing conditions described in IPCOM000125373D, to obtain the micronized voriconazole according to the present invention substantially as hereinbefore described. Preferably, the milling conditions comprise the following steps: (i) milling the voriconazole with undefined shape and/or crystal habit substantially as hereinbefore described; (ii) sieving the milled crystals through a screen of 250 µm or less; (iii) separating the sieved crystals; (iv) if there are non-sieved crystals remaining, repeating steps (i) to (iii); and (v) combining the sieved crystals. The milling preferably comprises pin-milling, and more preferably is carried out in a Stainless Steel pin mill working at 7,000 rpm. The screen of 250 µm or less is preferably a screen of 150 µm or less, and more preferably is a screen of 100 µm or less.

It is particularly preferred that voriconazole with substantially undefined crystal shape and/or crystal habit as referred to in step (a) is obtained by crystallizing voriconazole from a solvent system selected from the group consisting of isopropanol, methyl ethyl ketone/cyclohexane mixture, ethanol/cyclohexane mixture and dimethyl carbonate/cyclohexane mixture. Especially preferred is the use of isopropanol.

The present invention still further provides voriconazole suitable for pharmaceutical use and obtained by a process substantially as hereinbefore described. Still further there is provided use of voriconazole with substantially undefined crystal shape and/or crystal habit for preparing voriconazole substantially as hereinbefore described.

Mechanical particle size reduction, by for example micronizing or milling, of crystals of voriconazole with substantially undefined crystal shape advantageously provides voriconazole with a specific surface area ($S_W$) of between about 0.5 m$^2$/g to about 2 m$^2$/g, preferably of between about 0.9 m$^2$/g to about 1.7 m$^2$/g, substantially as hereinbefore described which is surprisingly much lower than the specific surface area of the micronized voriconazole described in IPCOM000125373D (i.e., 3 m$^2$/g to 5 m$^2$/g, preferably about 4 m$^2$/g). Additionally, the sphericity factor of the micronized voriconazole as provided according to the present invention is preferably in the range of about 0.20 to 0.70, preferably between 0.22 to 0.60. Thus, the micronized voriconazole of the invention has desirable flowability characteristics and is therefore particularly suitable for formulation. Finally, micronized voriconazole according to the present invention not only shows desirable and improved flowability properties as compared with the micronized voriconazole described in IPCOM000125373D, but also essentially shows the same solubility profile. Thus, although the specific surface area of the micronized voriconazole of the invention is lower than the specific surface area of the micronized voriconazole described in IPCOM000125373D and hence the micronized voriconazole of the invention should be expected to show worse solubility properties, the inventors have found that the solubility rate of micronized voriconazole according to the present invention is surprisingly similar to the solubility rate of the micronized voriconazole described in IPCOM000125373D. This is further illustrated by Example 10 and FIG. 4 below, from which it can be understood that in terms of solubility rate, the micronized voriconazole of the invention and micronized voriconazole described in IPCOM000125373D are substantially equivalent, despite the above discussed differences of specific surface area.

In terms of desirable solubility and/or dissolution as associated with voriconazole according to the present invention as referred to above, it is further preferred that there is provided voriconazole substantially as hereinbefore described, preferably characterized by one or more of a sphericity factor; a sphericity factor and a specific surface area; a sphericity factor, a specific surface area, and a Sauter diameter; and process of preparation again substantially as hereinbefore described, which is further characterized by a dissolution profile whereby at least 50% voriconazole is dissolved within 30 minutes from a test sample of about 100 mg of voriconazole, suspended or dissolved in 100 mL of water, at 25° C., pH 7.0, with stirring at 300 rpm. A dissolution profile as associated with voriconazole according to the present invention can preferably be still further characterized by reference to Example 10 and/or FIG. 4.

Micronized voriconazole in accordance with the present invention substantially as hereinbefore described (i.e., preferably characterized by one or more of a sphericity factor; a sphericity factor and a specific surface area; a sphericity factor, a specific surface area and a specific Sauter diameter; and preferably prepared by a mechanical comminution from large crystals of voriconazole with undefined crystal shape and/or crystal habit, as hereinbefore described) shows a number of improved properties as compared with prior art micronized voriconazole as described in IPCOM000125373D as follows.

Specifically, micronized voriconazole in accordance with the present invention substantially as hereinbefore described shows improved flowability properties. In this regard, the inventors have prepared pharmaceutical blends of micronized voriconazole of the present invention and of micronized voriconazole as described in IPCOM000125373D, both with the same qualitative and quantitative formula (i.e., containing 50 mg of micronized voriconazole and 50 mg of lactose monohydrate) and have found that the pharmaceutical blend containing the micronized voriconazole of the invention shows a Can Index value of 33 and a Hausner ratio value of 1.50, whereas the solid pharmaceutical blend containing prior art micronized voriconazole described in IPCOM000125373D shows a Can Index value of 48 and a Hausner ratio value of 1.92.

Compressibility index (or Can Index, hereinafter referred to as "CI") and the closely related Hausner ratio (hereinafter referred to as "HR") are well accepted methods for measuring the powder flow of a pharmaceutical powder (See European Pharmacopoeia 6.6, 2.9.36 Powder flow). The CI is a measure of the propensity of a powder to consolidate, and so it is a measure of the relative importance of inter-particulate interactions, which is especially relevant in poor flowing materials. Although the CI method cannot be used as a sole measure of powder flowability, it has the advantage of being simple to calculate, and it provides a quick comparison between API, excipients, and formulations (See Developing Solid Oral Dosage Forms Pharmaceutical Theory & Practice, Academic Press 2009. Y. Qiu, L. Liu, Y. Chen, G. G. Z. Zhang, W. Porter). The basic procedure to measure the CI and the HR is to measure the unsettled apparent volume, ($V_0$), and the final tapped volume, ($V_f$), of the powder after tapping the material until no further volume changes occur. The CI and the HR are calculated as follows:

$$\text{Compressibility Index (or Can Index)} = 100 \times [(V_0 - V_f)/V_0]$$

$$\text{Hausner ratio} = V_0/V_f$$

Alternatively, the CI and the HR can be calculated using measured values of bulk density ($\rho_{bulk}$) and tapped density ($\rho_{tapped}$), as follows:

Compressibility Index (or Carr Index)=$100\times[(\rho_{tapped}-\rho_{bulk})/\rho_{tapped}]$ Hausner ratio=$\rho_{tapped}/\rho_{bulk}$ For the CI and the HR, the generally accepted scale of flowability is given in Table 2.9.36.-2 of European Pharmacopoeia as follows:

| Compressibility index (percent) | Flow Character | Hausner Ratio |
| --- | --- | --- |
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very, very poor | >1.60 |

It can thus be understood from the above that although micronized voriconazole per se shows an inherent low flowability nature, a pharmaceutical blend containing micronized voriconazole of the present invention, and as such also micronized voriconazole per se of the present invention, show improved flowability properties, when respectively compared with a pharmaceutical blend containing prior art micronized voriconazole as described in IPCOM000125373D, and with prior art micronized voriconazole per se as described in IPCOM000125373D.

Also, the Can Index values obtained for the above blends additionally indicate that the micronized voriconazole in accordance with the present invention substantially as hereinbefore described shows improved compressibility characteristics compared to the above described prior art micronized voriconazole, which means that it shows better propensity to consolidate, and that hence is more suitable for tablet formation.

Additionally, micronized voriconazole in accordance with the present invention substantially as hereinbefore described shows similar Sauter diameter but a smaller specific surface area as compared with micronized voriconazole of the prior art, and therefore shows some improved properties, such as less chargeability. Drug substances in solid form can suffer electrostatic charging by contact or friction electrification (tribocharging) caused by interactions among particles or between particles and the surfaces that contain them. These interactions can affect formulation, manufacture, powder flow, and packing behaviour. In addition, it has been reported that electrostatic charges are also responsible for problems in blend uniformity. The net positive or negative tendency of dry powders to become charged electrostatically is called chargeability. There is no standard instrument for the measurement of the chargeability of dry powders (see *AAPS PharmSciTech* 2006, 7, Article 103). Triboelectric charge is commonly reported on a charge-to-mass basis since net charge and mass can be easily measured. However, triboelectric and induction charging are more closely related to the surface area of a particle rather to volume or mass (see S. L. Soo, *Instrumentation for fluid-particle flow*, Noyes Publications 1999, page 64). In this regard, it is well known that the surface area of the particles plays a key role in dry powder chargeability, and that therefore the particles having a higher specific surface area can hold a greater charge. Therefore, the crystals of micronized voriconazole according to the present invention exhibit a more reduced specific surface area and, consequently, also a reduced chargeability, as compared with prior art micronized voriconazole described in IPCOM000125373D.

There is also provided by the present invention a pharmaceutical composition comprising an effective amount of voriconazole substantially as hereinbefore described, together with a pharmaceutically acceptable carrier, diluent or excipient therefor. The term "effective amount" as used herein means an amount of voriconazole which is capable of preventing, ameliorating or eliminating a fungal infection, which fungal infection can be candidaemia in non-neutropenic patients, or invasive aspergillosis, or fluconazole-resistant invasive *Candida* infections, such as *C. krusei*, or caused by *Scedosporium* spp. and *Fusarium* spp. In certain cases, such fungal infections can be progressive infections. By "pharmaceutically acceptable carrier, diluent or excipient" is meant that the carrier, diluent or excipient must be pharmaceutically inactive and compatible with voriconazole and not be deleterious to a recipient thereof. Suitable pharmaceutically acceptable compositions according to the present invention are preferably solid compositions, such a powder or lyophilized product for inclusion in a suspension or dispersion for an injectable composition, or powder for an oral suspension, tablets, coated tablets such as film coated tablets, non coated tablets, orodispersible tablets, pellets, pills, granules, capsules, or mini-tablets in capsules; or liquid compositions, such as liquid parenteral or oral compositions in the form of a solution.

The solid pharmaceutical compositions comprising an effective amount of micronized voriconazole according to the present invention substantially as hereinbefore described (i.e., preferably characterized by one or more of a sphericity factor; a sphericity factor and a specific surface area; a sphericity factor, a specific surface area and a specific Sauter diameter; and preferably prepared by a mechanical comminution from large crystals of voriconazole with undefined crystal shape and/or crystal habit, as hereinbefore described) also show improved flowability properties as compared with prior art solid pharmaceutical compositions comprising an effective amount of micronized voriconazole as described in IPCOM000125373D as follows.

In this regard, the inventors have prepared, by means of direct compression process, solid pharmaceutical compositions of micronized voriconazole of the present invention and of prior art micronized voriconazole as described in IPCOM000125373D, both with the same qualitative and quantitative formula (i.e., containing 50 mg of micronized voriconazole and 50 mg of lactose monohydrate), have analyzed a number of parameters of the solid pharmaceutical formulation, and have found that the solid pharmaceutical composition containing the micronized voriconazole of the invention shows a uniformity of mass value of 62.9 mg, a deviation of mass uniformity value of 11.4 mg, and a percentage of non formation of the tablet of 9.52%, whereas the solid pharmaceutical composition containing prior art micronized voriconazole described in IPCOM000125373D shows a mass uniformity value of 6.9 mg, a deviation of mass uniformity value of 18.7 mg, and a percentage of non formation of the solid composition of 90.00%. These results indicate not only that the uniformity of mass of the solid pharmaceutical composition containing the micronized voriconazole of the invention is improved compared to the prior art, but also that the deviation in its preparation is lower, which in turn can be linked to improved flowability associated with voriconazole in accordance with the present invention.

Micronized voriconazole according to the present invention substantially as hereinbefore described (i.e., preferably characterized by one or more of a sphericity factor; a sphericity factor and a specific surface area; a sphericity factor, a specific surface area and a specific Sauter diameter; and preferably prepared by a mechanical comminution from large crystals of voriconazole with undefined crystal shape and/or crystal habit, as hereinbefore described) also surprisingly shows an improved solubility rate when included in a liquid composition as provided by the present invention, as compared with micronized voriconazole as described in IPCOM000125373D when included in a corresponding liquid composition.

In this regard, the inventors have prepared, under the same conditions, liquid pharmaceutical compositions of micronized voriconazole of the present invention and of prior art micronized voriconazole as described in IPCOM000125373D, both with the same qualitative and quantitative formula [i.e., 100 mL of formulation containing a concentration of 10.0 mg/mL of micronized voriconazole, 120.0 mg/mL of 2-hydroxypropyl-β-cyclodextrin (HPBCD), 20.8 mg/mL of glycine, and the sufficient quantity (q.s.) of water for injection], and have measured the solubility properties of the micronized voriconazole in said liquid pharmaceutical compositions. Surprisingly, the time for the total solution of the micronized voriconazole in said pharmaceutical solutions is much less for the pharmaceutical solution containing the micronized voriconazole of the invention (i.e., 60 minutes) as compared with the corresponding time for the pharmaceutical solution containing the micronized voriconazole as described in IPCOM000125373D (i.e., 109 minutes). Consequently, the solubility rate of the micronized voriconazole of the invention in said pharmaceutical solution is much higher than the solubility rate of the micronized voriconazole described in IPCOM000125373D (i.e., 16.67 mg/min as compared with 9.17 mg/min).

The present invention further provides voriconazole, or pharmaceutically acceptable salts or solvates thereof substantially as hereinbefore described, for use in the treatment of fungal infections as described above or for the manufacture of a medicament for the treatment of fungal infections as described above. The present invention also provides a method of treatment of a fungal infection, which method comprises administering to the patient an effective amount of voriconazole substantially as hereinbefore described.

The particle size parameters measured in the present invention have been obtained by means of laser light diffraction technique, and specifically by means of a Malvern Mastersizer S particle size analyzer having characteristics as set out below. Namely, the laser source used was a 2 milliwatt Helium/neon laser (633 nm wavelength); the detection system was a Fourier Transform lens system; the sample was run using a 2.40 mm lens; the sample unit was a sample unit for wet measurement, and particularly was a MS1-Small volume Sample Dispersion Unit stirred cell. The wet dispersion was prepared by using deionized water as a dispersant, and the dispersion was controlled by stirring the unit cell. Regarding the analyzed samples, these were prepared by wetting a weighed amount of voriconazole (approximately 250 mg) with a 0.1% solution of Tween 20 (20 mL) in deionized water; sonicating the sample for 2 minutes, delivering the sample dropwise to the previously background and corrected measuring cell filled with dispersant (deionized water) until the obscuration reached the desired level. The characterization parameters (volume distributions) were measured for at least six times for each sample, and the result is a mean of said measured values for each sample.

The specific surface area values disclosed in the present invention have been obtained by means of a specific surface area analysis technique based on the BET (Brunauer, Emmett and Teller) theory, which is a well-accepted theory known in the art for the calculation of surface areas of solids by means of measuring their physical adsorption of gas molecules (See S. Brunauer, P. H. Emmett and E. Teller, *J. Am. Chem. Soc.*, 1938, 60, 309). In particular, the specific surface area values measured in the present invention have been calculated from the BET surface area plot obtained by measuring the quantity of nitrogen gas molecules adsorbed by a weighted amount of solid at different relative pressures ($P/P_0$) within the range 0.05-0.3, at 77 K. Precisely, the measurement of the adsorption of gas molecules was carried out by means of a Micromeritics™ Gemini V equipment having the characteristics as set out below. Namely, the gas used for adsorption measure was nitrogen gas. The analyzed sample was prepared by weighting voriconazole (approximately 0.5 g). The sample for analysis was degassed (at 30° C. for 10 minutes and at 80° C. for one hour). The determination of the adsorption of nitrogen was measured at 77 K and for twelve relative pressures sufficiently dispersed within in the range of 0.05 to 0.3. (i.e. twelve absolute pressures in the range of 38.425 mmHg to 230.000 mmHg relative to a saturated pressure of 764,480 mmHg).

The particle density experimental values were obtained by means of a pycnometer, specifically a 50 mL glass pycnometer. The measurements were carried out under technical characteristics as set out below. Namely, the determinations were done at 25° C.; the liquid of reference was n-heptane; the measurements were carried out three times, and the result is the mean of said measured values.

The term "about" when used in the present invention preceding a number and referred to it, is meant to designate any value which lies within the range defined by the number ±10% of its value, preferably a range defined by the number ±5%, more preferably range defined by the number ±2%, still more preferably a range defined by the number ±1%. For example "about 10" should be construed as meaning within the range of 9 to 11, preferably within the range of 9.5 to 10.5, more preferably within the range of 9.8 to 10.2, and still more preferably within the range of 9.9 to 10.1.

The following examples further illustrate the invention but, of course, should not be construed as in any way limiting its scope.

EXAMPLES

Particle Size Distribution Method:

The particle size measurement for voriconazole was obtained using a Malvern Mastersizer S particle size analyzer equipped with a 2 milliwatt Helium/Neon laser and a Fourier Transform lens system. The sample was run using the 2.40 mm lens. The sample unit was a MS1-Small Volume Sample Dispersion Unit stirred cell. The dispersant was deionized water. The sample particle size distribution was assumed to follow a normal distribution.

Analysis model: polydisperse. Setup presentation: 3_WATERF. Particle R.I.=(1.6800, 0.01). Dispersant R.I.=1.33.

Samples for analysis were prepared by wetting a weighed amount of voriconazole (approximately 250 mg) with 20 mL of a 0.1% solution of Tween 20 in deionized water. This sample was sonicated for 2 minutes and delivered dropwise to the previously background and corrected measuring cell filled with dispersant (deionized water) until the obscuration reached the desired level. Volume distributions were obtained for at least six measures. For characterization, the values of $D_{10}$, $D_{50}$ and $D_{90}$ (by volume), D[4,3] (mean diameter by volume) and D[3,2] (mean diameter by surface area to volume, or Sauter diameter) were specifically listed, each one being the mean of the six values available for each characterization parameter.

The notation $D_X$ [also written as D(v, 0.X)] means that X % of the particles have a diameter less than a specified diameter D. Thus a $D_{90}$ [or D(v, 0.9)] of 100 μm means that 90% of the particles have a diameter less than 100 μm.

Optical Microscopy:

A solid sample (containing voriconazole crystals) was mounted on a slide and analyzed using an Olympus BX41 microscope. The micrographs were taken at 40× magnification.

Specific Surface Area Method:

The BET (Brunauer, Emmett and Teller) specific surface area for voriconazole was measured using a Micromeritics™ GEMINI V equipment (GEMINI CONFIRM V2.00 Software™). The sample for analysis was degassed at 30° C. for 10 minutes and at 80° C. for one hour. The determination of the adsorption of $N_2$ at 77 K was measured for relative pressures in the range of 0.02 to 0.2 for a weighed amount of voriconazole (i.e., approximately 0.5 g).

Density (Pycnometry):

Density of voriconazole samples was determined at 25° C. using a 50 mL glass pycnometer. A pre-weighted amount of about 1 g of voriconazole was introduced in the pycnometer, and the volume was filled with n-heptane, where voriconazole is practically insoluble at the working temperature. The density of the voriconazole sample ($\rho_S$) can be determined from the known density of n-heptane ($\rho_H$: 0.685 g/cm³), the weight of the pycnometer filled only with n-heptane)($W_H^0$), the weight of the filled pycnometer containing both voriconazole and n-heptane ($W_{S+H}$), and the weight of voriconazole ($W_S$):

$$\rho_S = \frac{W_S \cdot \rho_H}{W_H^0 + W_S - W_{S+H}}$$

Density of voriconazole samples was determined for three times, being the listed result the mean of the three values available for each sample.

X-ray Powder Diffraction (XRD):

The X-ray diffractogram was obtained using a RX SIEMENS D5000 diffractometer with a vertical goniometer and a copper anodic tube, radiation $CuK_\alpha$, λ=1, 54056 Å.

HPLC Method:

The chromatographic separation was carried out in a Symmetry C18, 3.5 μm, 4.6 mm×150 mm column.

The mobile phase A was a 0.010 M ammonium formate buffer, pH 4.0, which was prepared from 0.63 g of $HCOONH_4$ dissolved in 1000 mL of water, adjusting pH to 4.0 with formic acid. The mobile phase was mixed and filtered through a 0.22 μM nylon membrane under vacuum.

The mobile phase B was acetonitrile.

The chromatograph was programmed as follows:

Initial 0-13 min 75% mobile phase A, 13-25 min linear gradient to 40% mobile phase A, 25-35 min isocratic 40% mobile phase A, 35-40 min linear gradient to 25% mobile phase A, 40-55 min isocratic 25% mobile phase A, 55-60 min linear gradient to 75% mobile phase A and 60-65 min equilibration with 75% mobile phase A.

The chromatograph was equipped with a 254 nm detector and the flow rate was 1.0 mL/min at 20-25° C.

Solubility Rate Method:

About 100 mg of voriconazole was suspended in 100 mL of deionized water at 25° C., previously adjusted to pH 7.0 with diluted HCl or NaOH. The suspension was stirred at 300 rpm. Aliquots were taken and filtered after stirring times from 2 to 60 minutes. The amount of dissolved voriconazole in the aliquots was determined by HPLC and referred to the thermodynamic solubility value (100% solubility), as determined after stirring for at least 24 hours.

COMPARATIVE EXAMPLE 1

This comparative Example is a Reproduction of Example 1.2 of IPCOM000125373D, and prepares voriconazole in form of plate-like crystals.

Figure 5:
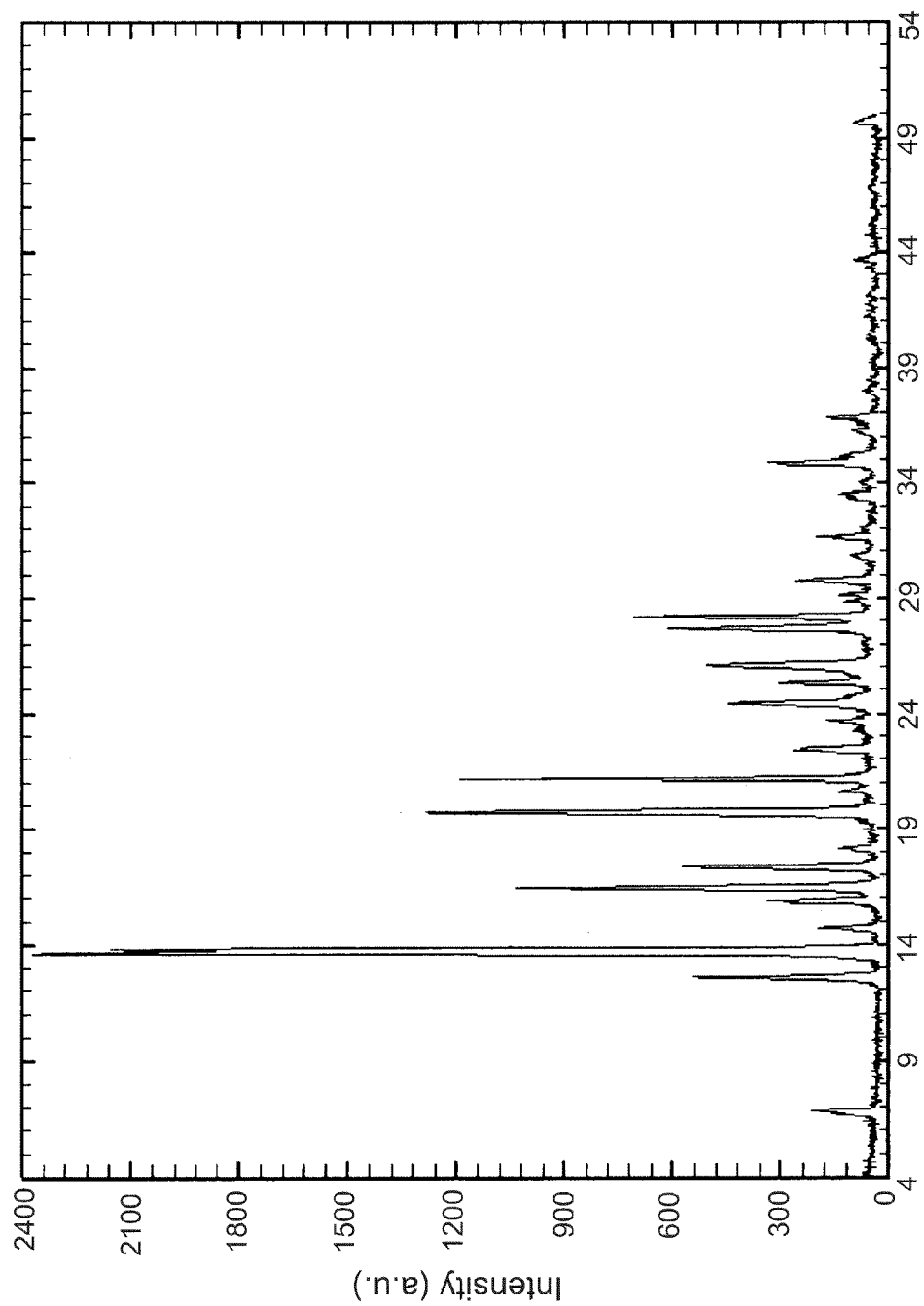
FIG. 5 depicts the X-ray powder diffractogram (XRD) of Voriconazole Form I as obtained in Comparative Example 1.

68 mL of absolute ethanol were added to 40 g of voriconazole. The suspension was heated to reflux temperature (about 80° C.) and the final solution was stirred at that temperature for 30 minutes. The mixture was cooled down to 20-25° C. in about 2 hours, stirred for 2 hours and the resulting suspension was filtered, washing the cake with two portions of 3 mL of ethanol. After drying, 34.02 g of a white solid was obtained (85% yield) corresponding to the product of the title. Optical microscopy: Plate-like crystals. XRD: Form I, see FIG. 5.

COMPARATIVE EXAMPLE 2

Figure 6:
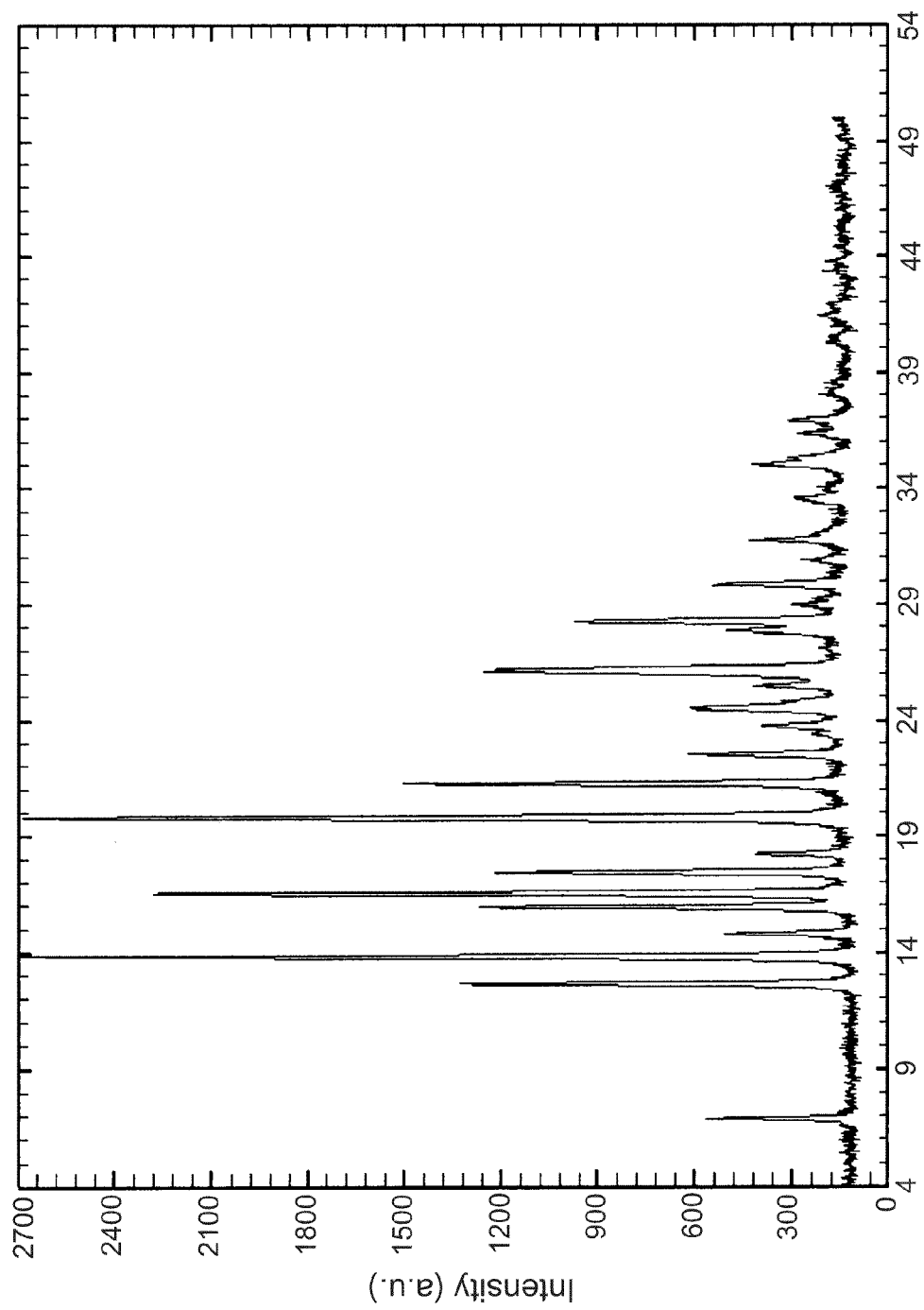
FIG. 6 depicts the X-ray powder diffractogram (XRD) of Voriconazole Form I as obtained in Comparative Example 2.

Voriconazole in form of plate-like crystals as obtained in Example 1 was micronized by using a Stainless Steel Rinajet micronizer working at 6 bar Venturi pressure and 5 bar mill pressure. Density: 1.40 g/cm³. Particle Size Distribution: $D_{50}$: 15.2 μm; D[4,3]: 28.7 μm; D[3,2]: 8.3 μm. XRD: Form I, see FIG. 6.

EXAMPLE 1

Figure 7:
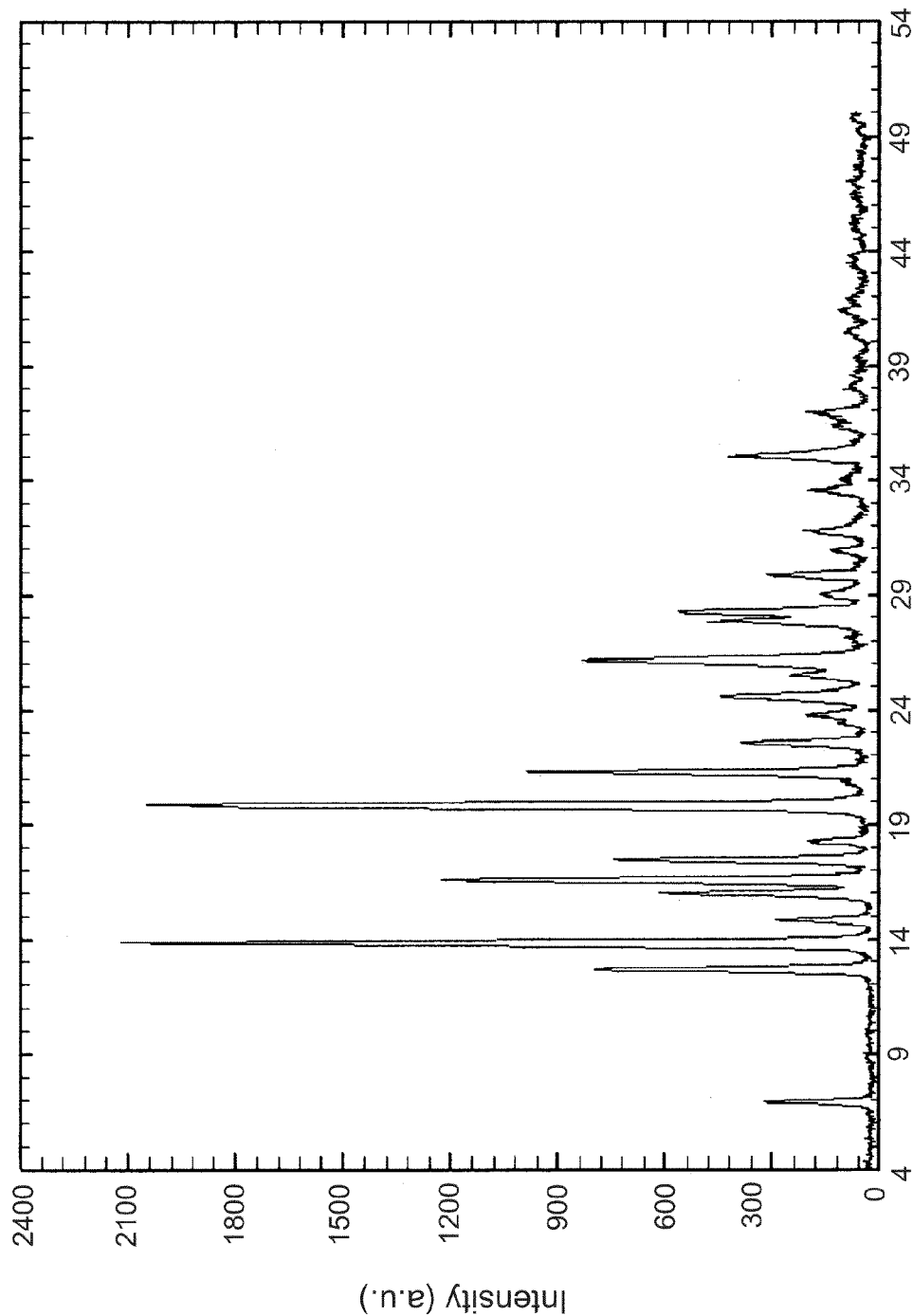
FIG. 7 depicts the X-ray powder diffractogram (XRD) of Voriconazole Form I as obtained in Example 1.
Figure 8:
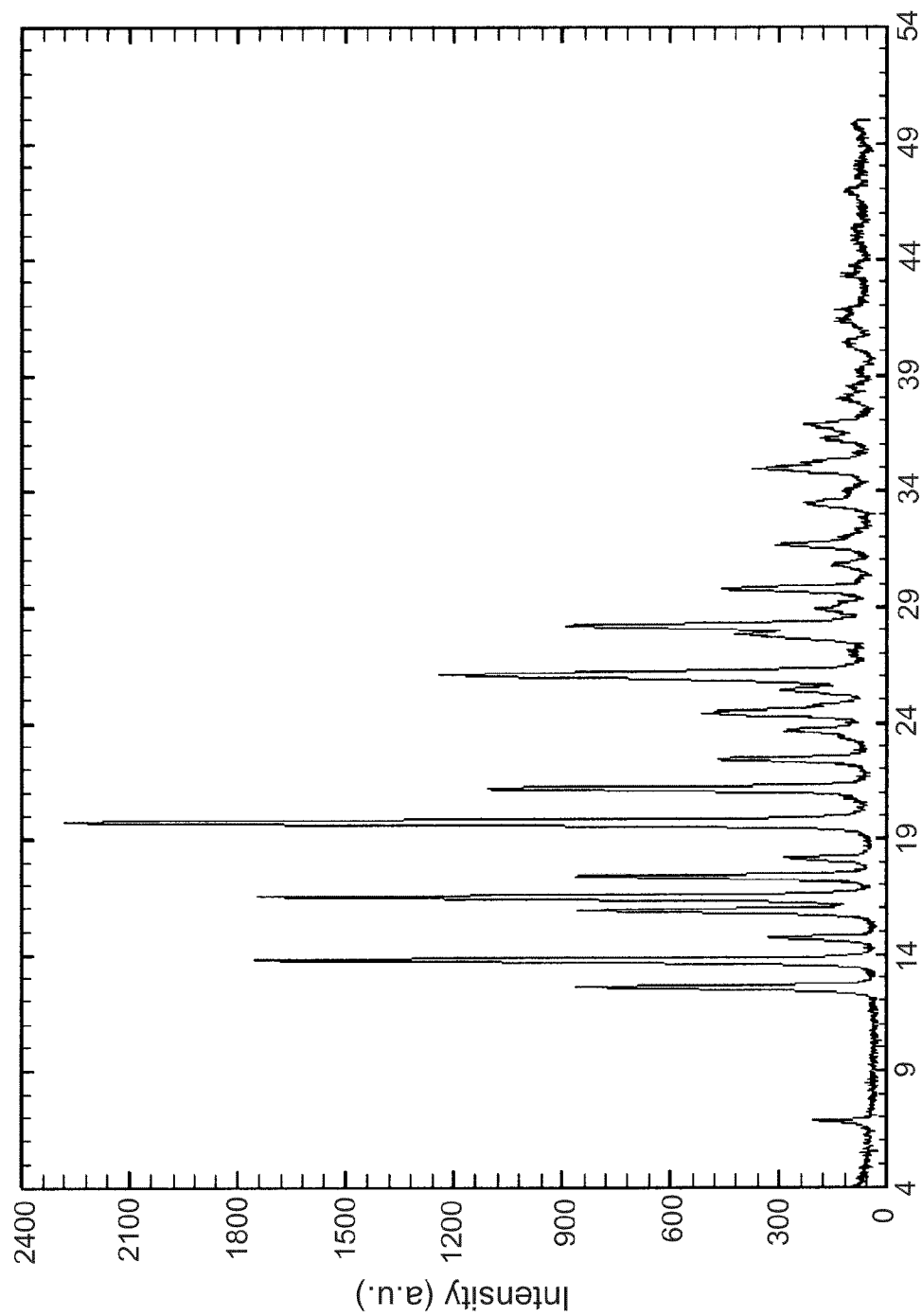
FIG. 8 depicts the X-ray powder diffractogram (XRD) of Voriconazole Form I as obtained in Example 3.

6.32 kg of voriconazole were dissolved with 16.6 L of isopropanol at reflux temperature. The solution was cooled down to 0-2° C. and stirred at that temperature for 1 hour. The resulting suspension was filtered, washing the cake with 2.5 L of isopropanol. After drying, 4.90 kg of a white solid was obtained (77.5% yield) corresponding to voriconazole. Optical microscopy: Crystals with undefined shape. XRD: Form I, see FIG. 7.

EXAMPLE 2

Voriconazole in form of crystals with undefined shape as obtained in Example 1 was micronized by using a Stainless Steel TL micronizer working at 5 bar Venturi pressure and 3 bar mill pressure. Density: 1.35 g/cm³. Particle Size Distribution: $D_{10}$: 7.4 μm, $D_{50}$: 29.7 μm, $D_{90}$: 102.8 μm; D[4,3]: 44.5 μm; D[3,2]: 15.4 μm. Specific Surface Area (BET): 0.9319 m²/g. Optical microscopy: Micronized product.

EXAMPLES 3-6

Voriconazole in form of crystals with undefined shape as obtained in Example 1 was micronized by using a Stainless Steel TL micronizer working at 5 bar Venturi pressure and 3 bar mill pressure.

Results for 4 different batches are summarized in Table 2.

TABLE 2

| Example | Density (g/cm³) | Particle Size Distribution (μm) | | | | | Specific Surface Area (m²/g) |
|---|---|---|---|---|---|---|---|
| | | $D_{10}$ | $D_{50}$ | $D_{90}$ | D[4, 3] | D[3, 2] | |
| 3 | 1.33 | 6.0 | 21.7 | 56.2 | 27.3 | 12.2 | 1.0997 |
| 4 | 1.32 | 6.0 | 22.4 | 64.0 | 30.3 | 12.3 | 1.0992 |

TABLE 2-continued

| Example | Density (g/cm³) | Particle Size Distribution (μm) | | | | | Specific Surface Area (m²/g) |
|---|---|---|---|---|---|---|---|
| | | $D_{10}$ | $D_{50}$ | $D_{90}$ | D[4, 3] | D[3, 2] | |
| 5 | 1.37 | 7.6 | 32.3 | 92.7 | 42.8 | 15.8 | 1.1451 |
| 6 | 1.40 | 8.6 | 33.4 | 92.3 | 43.3 | 17.2 | 0.9769 |

EXAMPLE 7

Voriconazole in form of crystals with undefined crystal shape as obtained in Example 1 was milled and sieved through a 100 μm screen. The sieved crystals were separated and the rest of crystals were milled and sieved again through a 100 μm screen. This milling and sieving was repeated with the rest of crystals (i.e., crystals not passing through the 100 μm sieve screen) until all crystals were sieved through the 100 μm screen. Finally, the sieved crystals were combined. The milling was carried out by using a Stainless Steel pin mill, working at 7,000 rpm. Particle Size Distribution: $D_{10}$: 7.5 μm, $D_{50}$: 25.3 μm, $D_{90}$: 57.4 μm; D[4,3]: 24.9 μm; D[3,2]: 14.3 μm; Specific Surface Area (BET): 1.1032 m²/g.

EXAMPLE 8

Voriconazole as obtained in Example 7 was micronized twice by using a Stainless Steel TL micronizer working at 7 bar Venturi pressure and 5 bar mill pressure. Particle Size Distribution: $D_{10}$: 2.5 μm, $D_{50}$: 7.3 μm, $D_{90}$: 29.9 μm; D[4,3]: 14.2 μm; D[3,2]: 5.2 μm; Specific Surface Area (BET): 1.5910 m2/g.

EXAMPLE 9

Sphericity factors for some batches of micronized voriconazole obtained from crystals with undefined shape are calculated using either the measured particle density value or the reported crystal density value and are summarized in Tables 3 and 4, respectively.

TABLE 3

| Example | ρ (g/cm³) | $D_{MVS}$ (μm) | $S_w$ (m²/g) | $\Psi_w$ |
|---|---|---|---|---|
| 2 | 1.35 | 15.4 | 0.9319 | 0.31 |
| 3 | 1.33 | 12.2 | 1.0997 | 0.34 |
| 4 | 1.32 | 12.3 | 1.0992 | 0.34 |
| 5 | 1.37 | 15.8 | 1.1451 | 0.24 |
| 6 | 1.40 | 17.2 | 0.9769 | 0.25 |

<sup>a</sup>Value calculated using the measured particle density value.

TABLE 4

| Example | ρ (g/cm³) | $D_{MVS}$ (μm) | $S_w$ (m²/g) | $^b\Psi_w$ |
|---|---|---|---|---|
| 2 | 1.442 | 15.4 | 0.9319 | 0.29 |
| 3 | 1.442 | 12.2 | 1.0997 | 0.31 |
| 4 | 1.442 | 12.3 | 1.0992 | 0.31 |
| 5 | 1.442 | 15.8 | 1.1451 | 0.23 |
| 6 | 1.442 | 17.2 | 0.9769 | 0.23 |
| 7 | 1.442 | 14.3 | 1.1032 | 0.26 |
| 8 | 1.442 | 5.2 | 1.5910 | 0.50 |

<sup>b</sup>Value calculated using the reported crystal density value.

As is recognized in the art and substantially as hereinbefore discussed, values for measured particle density are likely to have some variation from the above discussed exact characterizing value for density based on crystal structure, and a person skilled in the art would recognize that sphericity could be calculated based on either value. The inventors prefer, however, to base sphericity on the exact characterizing value for density based on crystal structure.

EXAMPLE 10

Figure 4:
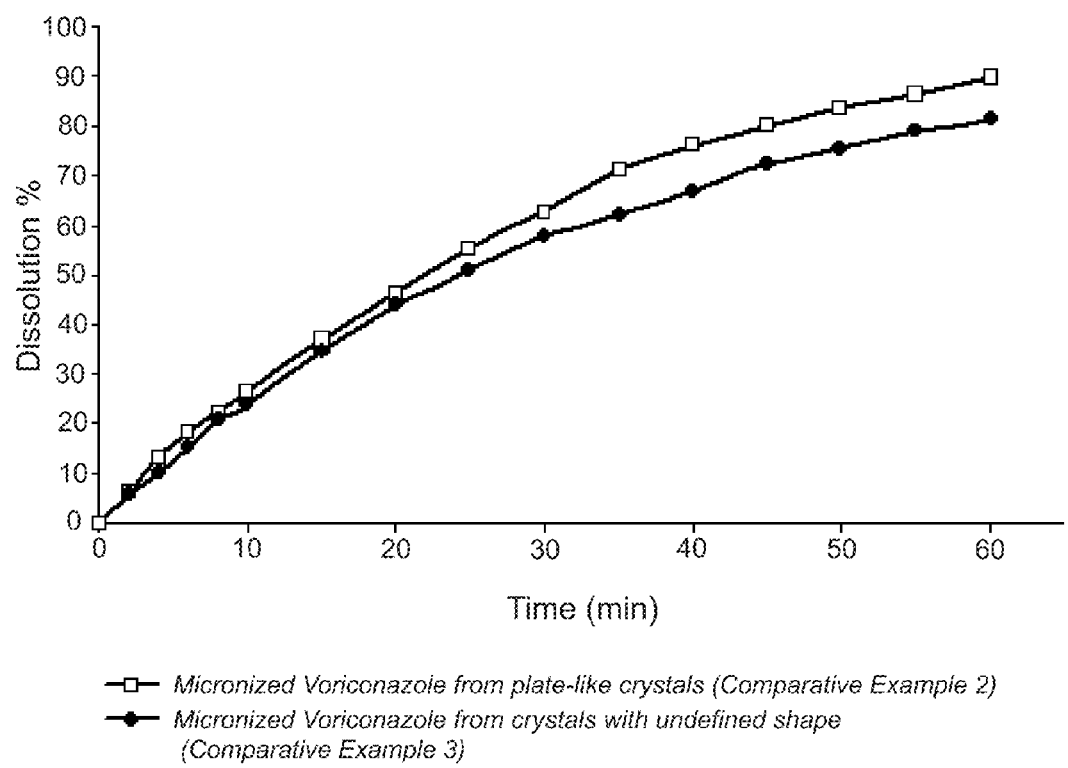
FIG. 4 depicts solubility rate plots as obtained in Example 10.

Solubility rate was tested for micronized voriconazole from plate-like crystals as obtained in Comparative Example 2 and micronized voriconazole from crystals with undefined shape as obtained in Example 3. Results are shown in FIG. 4.

EXAMPLE 11

Comparative studies of pharmaceutical blends comprising micronized voriconazole.

Pharmaceutical blends of micronized voriconazole and lactose monohydrate 1:1 were prepared as described in the following process: 1) weigh all the components: lactose monohydrate and micronized voriconazole; 2) sieve all the components through 0.8 mm sieve; and 3) mix in a laboratory blender, 15 minutes.

Flow property values evaluated through HR and CI were obtained from volume and density values obtained following a method based on the European Pharmacopeia. Results are shown in the following Table 5:

TABLE 5

| | Pharmaceutical blend comprising micronized voriconazole obtained in Example 8 and lactose monohydrate 1:1 | Pharmaceutical blend comprising micronized voriconazole obtained in Comparative Example 2 and lactose monohydrate 1:1 |
|---|---|---|
| Hausner Ratio (HR) | 1.5000 | 1.9231 |
| Carr Index (CI) | 33.33 | 48.00 |

EXAMPLE 12

Comparative studies of solid pharmaceutical compositions comprising micronized voriconazole.

Pharmaceutical compositions (i.e., tablets) of voriconazole and lactose monohydrate 1:1 were prepared as described in the following process: 1) weigh all the components: lactose monohydrate and micronized voriconazole; 2) sieve all the components through 0.8 mm sieve; 3) mix in a laboratory blender, 15 minutes; 4) compress by tabletting machine, 6 mm punches, target weight 100 mg±7.5%; and 5) adjust punches height by volume (calculation through density of the samples).

The results are obtained according to a method based on the European Pharmacopeia and are shown in the following Table 6:

TABLE 6

| | Pharmaceutical composition comprising micronized voriconazole obtained in Example 8 and lactose monohydrate 1:1 | Pharmaceutical composition comprising micronized voriconazole obtained in Comparative Example 2 and lactose monohydrate 1:1 |
|---|---|---|
| uniformity of mass | 62.9 mg | 6.9 mg |
| deviation | 11.4 mg | 18.7 mg |
| non formation of the tablet (%) | 9.52% | 90.00% |

EXAMPLE 13

Comparative studies of the preparation of liquid pharmaceutical compositions comprising micronized vorionazole.

Pharmaceutical solutions (100 mL) of micronized voriconazole were prepared having the following formula shown in following Table 7:

TABLE 7

| Component | Concentration |
| --- | --- |
| Micronized voriconazole | 10.0 mg/mL |
| Hydroxypropyl-β-cyclodextrin | 120.0 mg/mL |
| Glycine | 20.8 mg/mL |
| Water for injection | q.s. |

The above preparation was carried out by mixing the components in water under magnetic stirring and heating at 30±4° C. until total dissolution. Determination of the end point of total dissolution: visually (clear solution), and assay by HPLC (95-105%). Solubility results are shown in the following Table 8:

TABLE 8

|  | Pharmaceutical solution comprising micronized voriconazole as obtained in Example 8 | Pharmaceutical solution comprising micronized voriconazole obtained in Comparative Example 2 |
| --- | --- | --- |
| Time for total dissolution of micronized voriconazole | 60 minutes | 109 minutes |
| Solubility rate | 16.67 mg/min | 9.17 mg/min |

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. Voriconazole having a specific surface area of about 0.5 $m^2/g$ to about 2 $m^2/g$ and having a $D_{90}$ of less than about 150 µm.

2. Voriconazole according to claim 1, having a $D_{90}$ of less than about 100 µm.

3. Voriconazole according to claim 1, having a specific surface area of about 0.9 $m^2/g$ to about 1.7 $m^2/g$.

4. Voriconazole according to claim 3, having a $D_{90}$ of less than about 100 µm.

5. Voriconazole according to claim 1, formed by a method for mechanically reducing the particle size of voriconazole.

6. Voriconazole according to claim 5, wherein the method for mechanically reducing the particle size of voriconazole is selected from the group consisting of cutting, chipping, grinding, crushing, milling, micronizing, and triturating.

7. Voriconazole of claim 6, wherein the starting voriconazole used for the method for mechanically reducing the particle size of voriconazole selected from the group consisting of cutting, chipping, grinding, crushing, milling, micronizing, and triturating is voriconazole having a substantially undefined shape and/or crystal habit.

8. Voriconazole according to claim 2, formed by a method for mechanically reducing the particle size of voriconazole.

9. Voriconazole according to claim 8, wherein the method for mechanically reducing the particle size of voriconazole is selected from the group consisting of cutting, chipping, grinding, crushing, milling, micronizing, and triturating.

10. Voriconazole of claim 9, wherein the starting voriconazole used for the method for mechanically reducing the particle size of voriconazole selected from the group consisting of cutting, chipping, grinding, crushing, milling, micronizing, and triturating is voriconazole having a substantially undefined shape and/or crystal habit.

11. Voriconazole according to claim 3, formed by a method for mechanically reducing the particle size of voriconazole.

12. Voriconazole according to claim 11, wherein the method for mechanically reducing the particle size of voriconazole is selected from the group consisting of cutting, chipping, grinding, crushing, milling, micronizing, and triturating.

13. Voriconazole of claim 12, wherein the starting voriconazole used for the method for mechanically reducing the particle size of voriconazole selected from the group consisting of cutting, chipping, grinding, crushing, milling, micronizing, and triturating is voriconazole having a substantially undefined shape and/or crystal habit.

14. Voriconazole according to claim 4, formed by a method for mechanically reducing the particle size of voriconazole.

15. Voriconazole according to claim 14, wherein the method for mechanically reducing the particle size of voriconazole is selected from the group consisting of cutting, chipping, grinding, crushing, milling, micronizing, and triturating.

16. Voriconazole of claim 15, wherein the starting voriconazole used for the method selected from the group consisting of cutting, chipping, grinding, crushing, milling, micronizing, and triturating is voriconazole having a substantially undefined shape and/or crystal habit.

17. A process for preparing voriconazole of claim 1, said process comprising: (a) providing voriconazole with a substantially undefined shape and/or crystal habit; and (b) reducing the particle size of voriconazole with a substantially undefined shape and/or crystal habit with a method selected from the group consisting of cutting, chipping, grinding, crushing, milling, micronizing, and triturating.

18. A process according to claim 1, wherein the method is milling and said process comprises: (i) milling voriconazole having a substantially undefined shape and/or crystal habit; (ii) sieving the milled crystals through a screen having a diameter of 150 µm or less; (iii) separating the sieved crystals; (iv) combining the sieved crystals; and optionally repeating steps (i)-(iii) before step (iv).

19. The process of claim 18, wherein said milling comprises air-jet-milling or pin-milling.

20. A process for preparing voriconazole of claim 3, said process comprising: (a) providing voriconazole with a substantially undefined shape and/or crystal habit; and (b) reducing the particle size of voriconazole with a substantially undefined shape and/or crystal habit with a method selected from the group consisting of cutting, chipping, grinding, crushing, milling, micronizing, and triturating.

21. A process according to claim 20, wherein the method is milling and said process comprising the steps of: (i) milling voriconazole having a substantially undefined shape and/or crystal habit; (ii) sieving the milled crystals through a screen having a diameter of 150 μm or less; (iii) separating the sieved crystals; (iv) combining the sieved crystals; and optionally repeating steps (i)-(iii) before step (iv).

22. The process of claim 21, wherein said milling is comprises air-jet-milling or pin-milling.

23. The process according to claim 17, wherein the voriconazole with a substantially undefined shape and/or crystal habit of step (a) is obtained by crystallizing voriconazole from a solvent system selected from the group consisting of isopropanol, a mixture of methyl ethyl ketone and cyclohexane, a mixture of ethanol and cyclohexane, and a mixture of dimethyl carbonate and cyclohexane.

24. The process according to claim 20, wherein the voriconazole with a substantially undefined shape and/or crystal habit of step (a) is obtained by crystallizing voriconazole from a solvent system selected from the group consisting of isopropanol, a mixture of methyl ethyl ketone and cyclohexane, a mixture of ethanol and cyclohexane, and a mixture of dimethyl carbonate and cyclohexane.

25. A pharmaceutical composition comprising voriconazole according to claim 1, and one or more pharmaceutically acceptable excipients.

26. The pharmaceutical composition of claim 25, wherein the pharmaceutical composition is selected from the group consisting of a powder and a lyophilized product for inclusion in a suspension or dispersion for an injectable composition.

27. A pharmaceutical composition according to claim 25, which is selected from the group consisting of powder for an oral suspension, coated tablets, non coated tablets, orodispersible tablets, pellets, pills, granules, capsules, and mini-tablets in capsules.

28. A pharmaceutical composition comprising voriconazole according to claim 3, and one or more pharmaceutically acceptable excipients.

29. The pharmaceutical composition of claim 28, wherein the pharmaceutical composition is selected from the group consisting of a powder and a lyophilized product for inclusion in a suspension or dispersion for an injectable composition.

30. A pharmaceutical composition according to claim 28, which is selected from the group consisting of powder for an oral suspension, coated tablets, non coated tablets, orodispersible tablets, pellets, pills, granules, capsules, and mini-tablets in capsules.

31. A pharmaceutical composition according to claim 25, wherein the composition comprises a liquid composition.

32. A pharmaceutical composition according to claim 28, wherein the composition comprises a liquid composition.

33. A pharmaceutical composition formed from voriconazole according to claim 1, wherein said pharmaceutical composition further comprises one or more pharmaceutically acceptable excipients.

34. The pharmaceutical composition of claim 33, wherein the pharmaceutical composition is selected from the group consisting of a powder and a lyophilized product for inclusion in a suspension or dispersion for an injectable composition.

35. A pharmaceutical composition according to claim 33, which is selected from the group consisting of powder for an oral suspension, coated tablets, non coated tablets, orodispersible tablets, pellets, pills, granules, capsules, and mini-tablets in capsules.

36. A pharmaceutical composition formed from voriconazole according to claim 3, wherein said pharmaceutical composition further comprises one or more pharmaceutically acceptable excipients.

37. The pharmaceutical composition of claim 36, wherein the pharmaceutical composition is selected from the group consisting of a powder and a lyophilized product for inclusion in a suspension or dispersion for an injectable composition.

38. A pharmaceutical composition according to claim 36, which is selected from the group consisting of powder for an oral suspension, coated tablets, non coated tablets, orodispersible tablets, pellets, pills, granules, capsules, and mini-tablets in capsules.

39. A pharmaceutical composition according to claim 33, wherein the composition comprises a liquid composition.

40. A pharmaceutical composition according to claim 36, wherein the composition comprises a liquid composition.

* * * * *